(12) United States Patent
Rasmussen et al.

(10) Patent No.: US 8,377,672 B2
(45) Date of Patent: Feb. 19, 2013

(54) LIGAND FUNCTIONALIZED POLYMERS

(75) Inventors: Jerald K. Rasmussen, Woodville, WI (US); Catherine A. Bothof, Stillwater, MN (US); Kannan Seshadri, Woodbury, MN (US); Erin A. Satterwhite, West St. Paul, MN (US); Robert T. Fitzsimons, Minneapolis, MN (US); James I. Hembre, Plymouth, MN (US); Mahfuza B. Ali, Mendota Heights, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 133 days.

(21) Appl. No.: 12/986,485

(22) Filed: Jan. 7, 2011

(65) Prior Publication Data

US 2011/0201078 A1    Aug. 18, 2011

Related U.S. Application Data

(60) Provisional application No. 61/305,740, filed on Feb. 18, 2010.

(51) Int. Cl.
*C12N 9/00*  (2006.01)
*C12N 9/96*  (2006.01)
*C12N 7/06*  (2006.01)
*C08C 19/22* (2006.01)

(52) U.S. Cl. ........ 435/191; 525/376; 525/379; 525/381; 525/382; 526/310; 530/412; 530/421; 536/25.4; 435/183; 435/239; 435/252.1; 435/261; 435/325; 210/679; 210/735; 428/582

(58) Field of Classification Search .................. 525/376, 525/379, 381, 382; 526/310; 530/412, 421; 536/25.4; 435/183, 239, 252.1, 261, 325; 210/679, 735
See application file for complete search history.

(56) References Cited

U.S. PATENT DOCUMENTS

| | | | |
|---|---|---|---|
| 1,529,256 A | | 3/1925 | Kelley |
| 2,945,006 A | * | 7/1960 | Minsk .............................. 525/60 |
| 3,849,241 A | | 11/1974 | Butin et al. |
| 3,876,738 A | | 4/1975 | Marinaccio et al. |
| 3,928,517 A | | 12/1975 | Knight et al. |
| 4,118,531 A | | 10/1978 | Hauser |
| 4,157,418 A | | 6/1979 | Heilmann |
| 4,266,044 A | * | 5/1981 | Timmerman et al. ...... 525/328.2 |
| 4,339,473 A | | 7/1982 | D'Agostino et al. |
| 4,340,057 A | | 7/1982 | Bloch et al. |

(Continued)

FOREIGN PATENT DOCUMENTS

| | | |
|---|---|---|
| CA | 2422738 | 4/2002 |
| EP | 0 472 990 | 3/1992 |

(Continued)

OTHER PUBLICATIONS

Kolarz, Reactive & Functional Polymers, 36 (1998) 185-195.*

(Continued)

*Primary Examiner* — Robert C Boyle
(74) *Attorney, Agent, or Firm* — Kent S. Kokko (57) ABSTRACT

Ligand functionalized substrates, methods of making ligand functionalized substrates, and methods of using functionalized substrates are disclosed.

15 Claims, 1 Drawing Sheet

U.S. PATENT DOCUMENTS

| | | |
|---|---|---|
| 4,346,142 A | 8/1982 | Lazear |
| T103601 I4 | 11/1983 | Repetti |
| 4,473,474 A | 9/1984 | Ostreicher et al. |
| 4,529,256 A | 7/1985 | Kretzschmar et al. |
| 4,539,256 A | 9/1985 | Shipman |
| 4,563,388 A | 1/1986 | Bonk et al. |
| 4,618,533 A | 10/1986 | Steuck |
| 4,707,265 A | 11/1987 | Barnes, Jr. et al. |
| 4,726,989 A | 2/1988 | Mrozinski |
| 4,734,208 A | 3/1988 | Pall et al. |
| 4,773,903 A | 9/1988 | Weisman et al. |
| 4,837,067 A | 6/1989 | Carey, Jr. et al. |
| 4,845,132 A | 7/1989 | Masuoka et al. |
| 4,867,881 A | 9/1989 | Kinzer |
| 4,885,086 A | 12/1989 | Miura |
| 4,936,934 A | 6/1990 | Buehning |
| 4,944,879 A | 7/1990 | Steuck |
| 4,968,733 A | 11/1990 | Muller et al. |
| 4,981,730 A | 1/1991 | Zaleski |
| 4,985,298 A | 1/1991 | Buckley et al. |
| 5,006,247 A | 4/1991 | Dennison et al. |
| 5,061,751 A | 10/1991 | Patton |
| 5,064,866 A | 11/1991 | Toyomoto et al. |
| 5,071,880 A | 12/1991 | Sugo et al. |
| 5,075,342 A | 12/1991 | Ishigaki et al. |
| 5,120,594 A | 6/1992 | Mrozinski |
| 5,160,627 A | 11/1992 | Cussler et al. |
| 5,180,492 A | 1/1993 | Ohnishi et al. |
| 5,200,471 A | 4/1993 | Coleman et al. |
| 5,202,025 A | 4/1993 | Onishi et al. |
| 5,208,111 A | 5/1993 | Decher et al. |
| 5,209,849 A | 5/1993 | Hu et al. |
| 5,229,172 A | 7/1993 | Cahalan et al. |
| 5,260,360 A | 11/1993 | Mrozinski et al. |
| 5,282,971 A | 2/1994 | Degen et al. |
| 5,290,871 A | 3/1994 | Ahmed et al. |
| 5,308,641 A | 5/1994 | Cahalan et al. |
| 5,336,698 A | 8/1994 | Kashiwagi et al. |
| 5,342,688 A * | 8/1994 | Kitchin et al. ............... 428/32.3 |
| 5,344,701 A | 9/1994 | Gagnon et al. |
| 5,350,805 A | 9/1994 | Lin |
| 5,439,983 A | 8/1995 | Ahmed et al. |
| 5,453,467 A | 9/1995 | Bamford et al. |
| 5,458,782 A | 10/1995 | Hou et al. |
| 5,503,746 A | 4/1996 | Gagnon |
| 5,506,279 A | 4/1996 | Babu et al. |
| 5,531,900 A | 7/1996 | Raghavan et al. |
| 5,547,576 A | 8/1996 | Onishi et al. |
| 5,578,400 A | 11/1996 | Gineste et al. |
| 5,589,269 A | 12/1996 | Ali et al. |
| 5,623,044 A | 4/1997 | Chiao |
| 5,627,217 A | 5/1997 | Rilling et al. |
| 5,648,400 A | 7/1997 | Sugo et al. |
| 5,652,050 A | 7/1997 | Pall et al. |
| 5,712,027 A | 1/1998 | Ali et al. |
| 5,736,051 A | 4/1998 | Degen et al. |
| 5,773,485 A | 6/1998 | Bennett et al. |
| 5,782,908 A | 7/1998 | Cahalan et al. |
| 5,804,263 A | 9/1998 | Goldberg et al. |
| 5,846,438 A | 12/1998 | Pall et al. |
| 5,871,823 A | 2/1999 | Anders et al. |
| 5,902,836 A | 5/1999 | Bennett et al. |
| 5,906,734 A | 5/1999 | Girot et al. |
| 5,914,182 A | 6/1999 | Drumheller |
| 5,962,544 A | 10/1999 | Waller, Jr. |
| 6,033,719 A | 3/2000 | Keogh |
| 6,039,872 A | 3/2000 | Wu et al. |
| 6,056,529 A | 5/2000 | Meyering et al. |
| 6,063,484 A | 5/2000 | Exsted et al. |
| 6,096,293 A | 8/2000 | Stringer et al. |
| 6,096,369 A | 8/2000 | Anders et al. |
| 6,230,776 B1 | 5/2001 | Choi |
| 6,245,922 B1 | 6/2001 | Heilmann et al. |
| 6,258,276 B1 | 7/2001 | Mika et al. |
| 6,264,044 B1 | 7/2001 | Meyering et al. |
| 6,267,916 B1 | 7/2001 | Meyering et al. |
| 6,280,853 B1 | 8/2001 | Mickols |
| 6,287,730 B1 | 9/2001 | Callahan et al. |
| 6,315,130 B1 | 11/2001 | Olsen |
| 6,387,379 B1 | 5/2002 | Goldberg et al. |
| 6,391,200 B2 | 5/2002 | Pulek et al. |
| 6,413,070 B1 | 7/2002 | Meyering et al. |
| 6,448,301 B1 | 9/2002 | Gaddam et al. |
| 6,458,269 B1 | 10/2002 | Bassett et al. |
| 6,464,084 B2 | 10/2002 | Pulek |
| 6,506,847 B1 | 1/2003 | Song |
| 6,513,666 B2 | 2/2003 | Meyering et al. |
| 6,521,011 B1 | 2/2003 | Sundet et al. |
| 6,537,411 B1 | 3/2003 | Kang et al. |
| 6,596,167 B2 | 7/2003 | Ji et al. |
| 6,635,104 B2 | 10/2003 | Komkova et al. |
| 6,660,376 B1 | 12/2003 | Zimmel et al. |
| 6,669,994 B2 | 12/2003 | Swan et al. |
| 6,712,966 B1 | 3/2004 | Pulek et al. |
| 6,743,878 B2 | 6/2004 | Bowers et al. |
| 6,773,654 B2 | 8/2004 | Sugo et al. |
| 6,776,940 B2 | 8/2004 | Meyering et al. |
| 6,811,837 B2 | 11/2004 | Iwasa et al. |
| 6,818,038 B2 | 11/2004 | Sugo et al. |
| 6,828,386 B2 | 12/2004 | MacKinnon |
| 6,844,371 B1 | 1/2005 | Komatsu et al. |
| 6,852,802 B1 | 2/2005 | Komatsu et al. |
| 6,861,001 B2 | 3/2005 | Lee et al. |
| 6,939,466 B2 | 9/2005 | Pulek et al. |
| 7,048,855 B2 | 5/2006 | de la Cruz |
| 7,067,058 B2 | 6/2006 | Yeh et al. |
| 7,073,671 B2 | 7/2006 | Charkoudian |
| 7,094,469 B2 | 8/2006 | Moya |
| 7,112,389 B1 | 9/2006 | Arora et al. |
| 7,125,603 B2 | 10/2006 | David et al. |
| RE39,399 E | 11/2006 | Allen |
| 7,135,230 B2 | 11/2006 | Nakao et al. |
| 7,160,464 B2 | 1/2007 | Lee et al. |
| 7,169,933 B2 | 1/2007 | Benson et al. |
| 7,170,739 B1 | 1/2007 | Arora et al. |
| 7,178,676 B2 | 2/2007 | Pulek et al. |
| 7,204,997 B2 | 4/2007 | Bromberg et al. |
| 7,235,122 B2 | 6/2007 | Bryner et al. |
| 7,247,370 B2 | 7/2007 | Childs et al. |
| 7,294,743 B2 | 11/2007 | Algotsson et al. |
| 7,316,919 B2 | 1/2008 | Childs et al. |
| 7,338,692 B2 | 3/2008 | Smith et al. |
| 7,361,767 B2 | 4/2008 | Benson et al. |
| 7,374,416 B2 | 5/2008 | Cook et al. |
| 7,402,678 B2 | 7/2008 | Benson et al. |
| 7,604,746 B2 | 10/2009 | Childs et al. |
| 2002/0001834 A1 | 1/2002 | Keogh |
| 2004/0116026 A1 | 6/2004 | Kubose et al. |
| 2004/0116028 A1 | 6/2004 | Bryner |
| 2004/0203149 A1 | 10/2004 | Childs et al. |
| 2004/0242714 A1 | 12/2004 | Penezina et al. |
| 2005/0025911 A1 * | 2/2005 | Kasperchik et al. ......... 428/32.1 |
| 2005/0058821 A1 | 3/2005 | Smith et al. |
| 2005/0095266 A1 | 5/2005 | Perichaud et al. |
| 2005/0118425 A1 | 6/2005 | Childs et al. |
| 2005/0133441 A1 | 6/2005 | Charkoudian |
| 2005/0142296 A1 | 6/2005 | Lakshmi |
| 2005/0165167 A1 | 7/2005 | MacKinnon |
| 2005/0199335 A1 | 9/2005 | Oehl et al. |
| 2006/0016748 A1 | 1/2006 | Koguma et al. |
| 2006/0023487 A1 | 2/2006 | Fang et al. |
| 2006/0107639 A1 | 5/2006 | Hamlin et al. |
| 2006/0121217 A1 | 6/2006 | Childs et al. |
| 2006/0178070 A1 | 8/2006 | Kritzer et al. |
| 2007/0039874 A1 | 2/2007 | Kniajanski et al. |
| 2007/0042015 A1 | 2/2007 | Berry et al. |
| 2007/0065490 A1 | 3/2007 | Schabert et al. |
| 2007/0154651 A1 * | 7/2007 | Weiss et al. ................... 427/532 |
| 2007/0154703 A1 | 7/2007 | Waller et al. |
| 2007/0221569 A1 | 9/2007 | Stouffer et al. |
| 2008/0017578 A1 | 1/2008 | Childs et al. |
| 2008/0193981 A1 | 8/2008 | Fahrner et al. |
| 2008/0230471 A1 | 9/2008 | Tamada et al. |
| 2008/0264867 A1 | 10/2008 | Mika et al. |
| 2009/0020472 A1 | 1/2009 | Lucas et al. |
| 2009/0032463 A1 | 2/2009 | Childs et al. |
| 2009/0035552 A1 | 2/2009 | Childs et al. |

| | | | |
|---|---|---|---|
| 2009/0098359 | A1 | 4/2009 | Waller, Jr. et al. |
| 2009/0176052 | A1 | 7/2009 | Childs et al. |
| 2010/0075131 | A1 | 3/2010 | Seshadri et al. |
| 2010/0075560 | A1 | 3/2010 | Seshadri et al. |
| 2010/0320138 | A1 | 12/2010 | Waller et al. |
| 2011/0033633 | A1 | 2/2011 | Bothof et al. |

FOREIGN PATENT DOCUMENTS

| | | |
|---|---|---|
| EP | 0 632 329 | 1/1995 |
| EP | 0 779 387 | 6/1997 |
| EP | 0 860 213 | 8/1998 |
| EP | 1 228 756 | 8/2002 |
| EP | 1 552 878 | 7/2005 |
| EP | 2027921 | 2/2009 |
| EP | 2 036 930 | 3/2009 |
| JP | 62298405 | 12/1987 |
| JP | 63240902 | 10/1988 |
| JP | 5111607 | 5/1993 |
| JP | 08290066 | 11/1996 |
| JP | 10085572 | 4/1998 |
| JP | 10279713 | 10/1998 |
| JP | 2002371471 | 12/2002 |
| JP | 2003301059 | 10/2003 |
| JP | 2004073943 | 3/2004 |
| WO | WO 89/09246 | 10/1989 |
| WO | WO 97/18904 | 5/1997 |
| WO | WO 00/01468 | 1/2000 |
| WO | WO 00/22032 | 4/2000 |
| WO | WO 00/54866 | 9/2000 |
| WO | WO 01/96487 | 12/2001 |
| WO | WO 02/060509 | 8/2002 |
| WO | WO 03/008011 | 1/2003 |
| WO | WO 2004/002714 | 1/2004 |
| WO | WO 2005/035641 | 4/2005 |
| WO | WO 2005/040092 | 5/2005 |
| WO | WO 2007/001405 | 1/2007 |
| WO | WO 2007/078878 | 7/2007 |
| WO | WO 2007/078880 | 7/2007 |
| WO | WO 2008/008872 | 1/2008 |
| WO | WO 2008/153744 | 12/2008 |
| WO | WO 2009/085726 | 7/2009 |
| WO | WO 2009/086347 | 7/2009 |
| WO | WO 2009/127285 | 10/2009 |
| WO | WO 2009/146321 | 12/2009 |
| WO | WO 2009/148869 | 12/2009 |
| WO | WO 2010/033794 | 3/2010 |
| WO | WO 2010/033807 | 3/2010 |

OTHER PUBLICATIONS

PCT International Search Report, PCT/US2011/024960.
U.S. Appl. No. 61/057,517 entitled, "Method of Making Ligand Functionalized Substrates" filed May 30, 2008.
U.S. Appl. No. 61/057,523 entitled, "Ligand Functionalized Substrates" filed May 30, 2008.
U.S. Appl. No. 12/819,261 entitled, "Funtionalized Nonwoven Article" filed Jun. 21, 2010.
U.S. Appl. No. 61/098,337 entitled, "Ligand Graft Functionalized Substrates" filed Sep. 19, 2008.
U.S. Appl. No. 61/219,497 entitled, "Functionalized Nonwoven Article" filed Jun. 23, 2009.
U.S. Appl. No. 12/562,381 entitled, "Ligand Graft Functionalized Substrates" filed Sep. 18, 2009.
Barner, L., et al., "Reversible Addition-Fragmentation Chain Transfer Graft Copolymerization of Styrene and m-Isopropenyl-α, α'-dimethylbenzyl Isocyanate from Polypropylene Lanterns: Solid Phases for Scavenging Applications." Journal of Polymer Science: Part A: Polymer Chemistry, vol. 44, 2006, pp. 857-864.
Barsbay, M. et al., "Verification of Controlled Grafting of Styrene from Cellulose via Radiation-Induced RAFT Polymerization," Macromolecules, vol. 40, No. 20, 2007, pp. 7140-7147.
Bolto et al., "Organic polyelectrolytes in water treatment," Water Research, vol. 41, pp. 2301-2324, (2007).
Buehler et al., "Solvent Effects on the Permeability of Membrane-Supported Gels," Ind. Eng. Chem. Res., vol. 41, No. 3, pp. 464-472, (2002).

Burke, J., "Solubility Parameters: Theory and Application," AIC Book and Paper Group Annual, vol. 3, (1984), pp. 13-58.
Chen, J., et al., "Grafting copolymerization of acrylamides onto preirradiated PP Films," Radiation Physics and Chemistry, vol. 55, (1999), pp. 87-92.
Childs, et al., "Nanofiltration using pore-filled membranes: effect of polyelectrolyte composition on performance", Separation and Purification Technology; 22-23 (2001), pp. 507-517.
Davies, "The Separation of Airborne Dust and Particles," The Institution of Mechanical Engineers, Proceedings (B), vol. 1B, Nos. 1-12, pp. 185-213, (1952-1953).
DuPont™ brochure entitled, "DuPont™ Hybrid Membrane Technology—Nanofiber Science to Revolutionize Filtration, Energy Storage and Beyond," Copyright © 2007, 4 pages.
Franken, A. et al., "Wetting Criteria for the Applicability of Membrane Distillation," Journal of Membrane Science, vol. 33, (1987), pp. 315-328.
Ghosh, "Protein separation using membrane chromatography: opportunities and challenges," Journal of Chromatography A., vol. 952, Issues 1-2, pp. 13-27, Apr. 5, 2002.
Grasselli, M. et al., "Electron-beam induced RAFT-graft polymerization of poly(acrylic acid) onto PVDF," Nuclear Instruments and Methods in Physics Research B, vol. 236, 2005, pp. 202-207.
Gupta, B., et al., Preirradiation grafting of acrylonitrile onto polypropylene monofilament for biomedical applications: I. Influence of synthesis conditions, Radiation Physics and Chemistry, vol. 75, (2006), pp. 161-167.
Ito, et al., "pH-Sensitive Gating by Conformational Change of a Polypeptide Brush Grafted onto a Porous Polymer Membrane," Journal of the American Chemical Society, vol. 119, pp. 1619-1623, (1997).
Jianqin, L., et al., "Pre-irradiation grafting of temperature sensitive hydrogel on cotton cellulose fabric," Radiation Physics and Chemistry, vol. 55, (1999), pp. 55-59.
Kanani et al., "Separation of human plasma proteins HAS and HIgG using high-capacity macroporous gel-filled membranes," Biochemical Engineering Journal, vol. 35, pp. 295-300, (2007).
Kanani, et al., "Protein bioseparation by membrane chromatography using polyelectrolyte gel-coated adsorptive membranes," Department of Chemical Engineering, McMaster University, 7 pages.
Kavakli, et al., "Radiation-induced grafting of dimethylaminoethylmethacrylate onto PE/PP nonwoven fabric," Science Direct, Nuclear Instruments and Methods in Physics Research B, vol. 265, pp. 204-207, (2007).
Kawai et al., "Protein binding to polymer brush, based on ion-exchange, hydrophobic, and affinity interactions," Journal of Chromatography B, vol. 790, Issues 1-2, pp. 131-142, Jun. 25, 2003.
Kiani, K., et al., "Raft Mediated Surface Grafting of t-Butyl Acrylate onto an Ethylene-Propylene Copolymer Initiated by Gamma-Radiation," Journal of Polymer Science: Part A: Polymer Chemistry, vol. 45, 2007, pp. 1074-1083.
Kim et al., "Diffusion and Flow through Polymer-Lined Micropores," Ind. Eng. Chem. Res., vol. 30, pp. 1008-1016, (1991).
Latulippe, et al., "Characterization of Gel-Filled Membranes for Plasma Protein Fractionation," Department of Chemical Engineering, McMaster University, 4 pages.
Mika et al., "Acid/base properties of poly(4-vinylpyridine) anchored within microporous membranes," Journal of Membrane Science, vol. 152, pp. 129-140, (1999).
Mika et al., "Chemical valves based on poly(4-vinylpyridine)-filled microporous membranes," Journal of Membrane Science, vol. 153, pp. 45-56, (1999).
Mika et al., "Porous, polyelectrolyte-filled membranes: Effect of cross-linking on flux and separation", Journal of Membrane Science, 135 (1997), pp. 81-92.
Mika et al., "Salt separation and hydrodynamic permeability of porous membrane filled with pH-sensitive gel," Journal of Membrane Science, vol. 206, pp. 19-30, (2002).
Mika, et al., "A new class of polyelectrolyte-filled microfiltration membranes with environmentally controlled porosity", Journal of Membrane Science, 108 (1995) pp. 37-56.

Mika, et al., "Poly(4-vinylpyridine)-filled microfiltration membranes: physicochemical properties and morphology", Journal of Membrane Science, 136 (1997), pp. 221-232.

Nho, Y., et al., "Grafting polymerization of styrene onto preirradiated polypropylene fabric," Radiation and Physics and Chemistry, vol. 54, (1999), pp. 317-322.

Osada et al., "Control of Water Permeability by Mechanochemical Contraction of Poly(Methacrylic Acid)-Grafted Membranes," Journal of Membrane Science, vol. 27, pp. 327-338, (1986).

Pietrucha, K., "Effect of Chain Transfer Agent on the Radiation Grafting of Methyl Methacrylate Onto Chromium (III) Crosslinked Collagen," Journal of Radioanalytical and Nuclear Chemistry, vol. 149, No. 2, (1991), pp. 327-331.

Riske, et al., "The use of chitosan as a flocculant in mammalian cell culture dramatically improves clarification throughput without adversely impacting monoclonal antibody recover," Journal of Biotechnology, vol. 128, pp. 813-823, (2007).

Shaozao, T., et al., "Effect of Gamma Ray Irradiation on Properties of Polypropylene Fibers and Nonwoven Fabrics," vol. 22, No. 6, (1999), pp. 18-21.

Suryanarayan et al., "The effect of gel layer thickness on the salt rejection performance of polyelectrolyte gel-filled nanofiltration membranes," Journal of Membrane Science, vol. 290, pp. 196-206, (2007).

Ulbricht et al., "Porous Polypropylene Membranes with Different Carboxyl Polymer Brush Layers for Reversible Protein Binding via Surface-Initiated Graft Copolymerization," Chem. Mater, vol. 17, No. 10, pp. 2622-2631, (2005).

Ulbricht, "Advanced functional polymer membranes," Polymer, vol. 47, pp. 2217-2262, (2007).

Wente et al., "Manufacture of Superfine Organic Fibers," Navel Research Laboratories Report No. 4364, (1954).

Wente, "Superfine Thermoplastic Fibers," Industrial and Engineering Chemistry, Naval Research Laboratory, vol. 48, No. 8, pp. 1342-1346, (1956).

Winnik et al., "Polyacrylic acid pore-filled microporous membranes and their use in membrane-mediated synthesis of nanocrystalline ferrihydrite," Can. J. Chem., vol. 76, pp. 10-17, (1998).

Zazzera et al., "XPS and SIMS Study of Anhydrous HF and UV/Ozone-Modified Silicon (100) Surfaces," J. Electrochem. Soc., vol. 136, No. 2, (1989), pp. 484-491.

Zhang et al., "pH Control of Transport through a Porous Membrane Self-Assembled with a Poly(acrylic acid) Loop Brush," Langmuir, vol. 17, pp. 8336-8340, (2001).

Zhou et al., "Pore-filled nanofiltration membranes based on poly(2-acrylamido-2-methylpropanesulfonic acid) gels," Journal of Membrane Science, vol. 254, pp. 89-99, (2005).

* cited by examiner

LIGAND FUNCTIONALIZED POLYMERS

CROSS REFERENCE TO RELATED APPLICATION

This application claims the benefit of U.S. Provisional Patent Application No. 61/305,740, filed Feb. 18, 2010, the disclosure of which is incorporated by reference herein in its entirety.

TECHNICAL FIELD

The present disclosure relates to ligand-functionalized polymers, and methods for preparing the same. The functionalized polymers are useful in selectively binding and removing biological materials, such as viruses, from biological samples.

BACKGROUND

Detection, quantification, isolation and purification of target biomaterials, such as viruses and biomacromolecules (including constituents or products of living cells, for example, proteins, carbohydrates, lipids, and nucleic acids) have long been objectives of investigators. Detection and quantification are important diagnostically, for example, as indicators of various physiological conditions such as diseases. Isolation and purification of biomacromolecules are important for therapeutic uses and in biomedical research. Biomacromolecules such as enzymes which are a special class of proteins capable of catalyzing chemical reactions are also useful industrially; enzymes have been isolated, purified, and then utilized for the production of sweeteners, antibiotics, and a variety of organic compounds such as ethanol, acetic acid, lysine, aspartic acid, and biologically useful products such as antibodies and steroids.

In their native state in vivo, structures and corresponding biological activities of these biomacromolecules are maintained generally within fairly narrow ranges of pH and ionic strength. Consequently, any separation and purification operation must take such factors into account in order for the resultant, processed biomacromolecule to have potency.

The use of certain ionic polymers, especially cationic polymers, for the flocculation of cell and/or cell debris, as well as for the precipitation of proteins, is known. Similarly, ionic polymers have been used to modify filtration media to enhance the removal of impurities from process streams in depth filtration or membrane absorber type applications. The effectiveness of these flocculants is typically reduced as the conductivity of the media being processed increases, i.e. as the salt content increases. There is a need in the art for polymeric materials with increased affinity for biological species under high ionic strength conditions.

Chromatographic separation and purification operations can be performed on biological product mixtures, based on the interchange of a solute between a moving phase, which can be a gas or liquid, and a stationary phase. Separation of various solutes of the solution mixture is accomplished because of varying binding interactions of each solute with the stationary phase; stronger binding interactions generally result in longer retention times when subjected to the dissociation or displacement effects of a mobile phase compared to solutes which interact less strongly and, in this fashion, separation and purification can be effected.

Most current capture or purification chromatography is done via conventional column techniques. These techniques have severe bottlenecking issues in downstream purification, as the throughput using this technology is low. Attempts to alleviate these issues include increasing the diameter of the chromatography column, but this in turn creates challenges due to difficulties of packing the columns effectively and reproducibly. Larger column diameters also increase the occurrence of problematic channeling. Also, in a conventional chromatographic column, the absorption operation is shut down when a breakthrough of the desired product above a specific level is detected. This causes the dynamic or effective capacity of the adsorption media to be significantly less than the overall or static capacity. This reduction in effectiveness has severe economic consequences, given the high cost of some chromatographic resins.

Polymeric resins are widely used for the separation and purification of various target compounds. For example, polymeric resins can be used to purify or separate a target compound based on the presence of an ionic group, based on the size of the target compound, based on a hydrophobic interaction, based on an affinity interaction, or based on the formation of a covalent bond. There is a need in the art for polymeric substrates having enhanced affinity for viruses to allow selective removal from a biological sample. There is further need in the art for ligand functionalized membranes that overcome limitations in diffusion and binding, and that may be operated at high throughput and at lower pressure drops.

SUMMARY OF THE INVENTION

The present invention is directed to ligand-functionalized polymers, and methods of making the same. More specifically, the ligand-functionalized polymer includes a base polymer, having carbonyl functional groups, which has been modified to provide grafted ligand groups having the requisite affinity for binding neutral or negatively charged biomaterials, such as cells, cell debris, bacteria, spores, viruses, nucleic acids, and proteins.

In some embodiments, the ligand-functionalized polymer may be used as a flocculant whereby a biological sample, such as a cell culture fluid, is contacted causing negative and/or neutral species to bind to the polymer and precipitate from the solution or suspension. In another embodiment, a base substrate, such as a microporous membrane or a particle, may be coated with the ligand-functionalized polymer. In another embodiment, the ligand-functionalized polymer may be grafted to the surface of a base substrate.

The ligand functionalized polymer may be described as the reaction product of a carbonyl-functional polymer, such as diacetone (meth)acrylate (co)polymer, and a ligand compound of Formula I:

wherein
$R^2$ is a covalent bond, a $C_2$ to $C_{12}$ alkylene, a $C_5$-$C_{12}$ (hetero)arylene, $R^9$ is $C_2$ to $C_{12}$ alkylene or $C_5$-$C_{12}$ (hetero)arylene,
each $R^3$ is independently H, —OH, $C_1$-$C_{12}$ alkyl, or $C_5$-$C_{12}$ (hetero)aryl, preferably H or $C_1$-$C_4$ alkyl,
$R^4$ is H, $C_1$-$C_{12}$ alkyl, $C_5$-$C_{12}$ (hetero)aryl, or —N($R^3$)$_2$, preferably H, or $C_1$-$C_4$ alkyl.

Methods of making a ligand functionalized substrate are provided. In some embodiments, the method comprises reacting a carbonyl-functional polymer with the ligand compound of Formula I, optionally in the presence of an acid catalyst.

A functionalized polymer is provided having grafted pendent ligand groups, said ligand groups of Formula II:

II wherein
$R^1$ is H, $C_1$-$C_{12}$ alkyl, or $C_5$-$C_{12}$ (hetero)aryl, preferably $C_1$-$C_{12}$ alkyl;
$R^2$ is a covalent bond, a $C_2$ to $C_{12}$ alkylene, or a $C_5$-$C_{12}$ (hetero)arylene, $R^9$ is $C_2$ to $C_{12}$ alkylene or $C_5$-$C_{12}$ (hetero)arylene,
each $R^3$ is independently H, —OH, $C_1$-$C_{12}$ alkyl, or $C_5$-$C_{12}$ (hetero)aryl, preferably H or $C_1$-$C_4$ alkyl,
$R^4$ is H, $C_1$-$C_{12}$ alkyl, $C_5$-$C_{12}$ (hetero)aryl, or —N($R^3$)$_2$, preferably H, or $C_1$-$C_4$ alkyl.

It will be recognized that the group of Formula II is the linkage formed between the terminal amine of the ligand compound of Formula I and the carbonyl group of the carbonyl-functional polymer. With respect to the above Formula II, the "~" represents a covalent bond or an organic linking group interposed between the ligand group and polymer chain.

In other embodiments, ligand functional polymer may be prepared in which the imine linking group (~~C($R^1$)=N—) is reduced to an amine linking group (~~CH($R^1$)—NH—). This may be effected by treating the extant ligand functional polymer with a reducing agent, such as sodium cyanoborohydride, or the reduction may be effected in situ by added the reducing agent to the reaction mixture of the carbonyl functional polymer and the compound of Formula I.

In this application, (meth)acrylic is inclusive of both methacrylic and acrylic.

As used herein, "alkyl" or "alkylene" includes straight-chained, branched, and cyclic alkyl groups and includes both unsubstituted and substituted alkyl groups. Unless otherwise indicated, the alkyl groups typically contain from 1 to 20 carbon atoms. Examples of "alkyl" as used herein include, but are not limited to, methyl, ethyl, n-propyl, n-butyl, n-pentyl, isobutyl, t-butyl, isopropyl, n-octyl, n-heptyl, ethylhexyl, cyclopentyl, cyclohexyl, cycloheptyl, adamantyl, and norbornyl, and the like. Unless otherwise noted, alkyl groups may be mono- or polyvalent.

As used herein, "aryl" or "arylene" is an aromatic group containing 5-12 ring atoms and can contain optional fused rings, which may be saturated, unsaturated, or aromatic. Examples of an aryl groups include phenyl, naphthyl, biphenyl, phenanthryl, and anthracyl. Heteroaryl is aryl containing 1-3 heteroatoms such as nitrogen, oxygen, or sulfur and can contain fused rings. Some examples of heteroaryl groups are pyridyl, furanyl, pyrrolyl, thienyl, thiazolyl, oxazolyl, imidazolyl, indolyl, benzofuranyl, and benzthiazolyl. Unless otherwise noted, aryl and heteroaryl groups may be mono- or polyvalent.

DETAILED DESCRIPTION OF THE INVENTION

In the article and methods of this invention, ligand-functionalized polymers are provided which have enhanced affinity, especially in high ionic strength media, for neutral or negatively charged biological materials such as host cell proteins, DNA, RNA, viruses, and other microorganisms. The affinity for such biomaterials allows positively charged materials, such as antibodies, to be purified, as they are not bound to the ligand functional groups. The ligand functionalized substrate allows the selective capture or binding of target biomaterials by the ligand groups, while other materials, lacking the affinity for the ligand groups are passed. In some embodiments the ligand functionalized polymer is used as a flocculant to selectively bind target biomaterials, precipitate them from solution, and the precipitated adduct subsequently separated.

The base polymer comprises a carbonyl-functional (co)polymer; i.e. a polymer having aldehyde or ketone groups, typically pendent from the polymer chain. The polymers comprise polymerized monomer units of an ethylenically unsaturated monomer having a carbonyl group, preferably a ketone group, or copolymerized monomer units of an ethylenically unsaturated monomer and carbon monoxide (Carbon monoxide copolymers).

Generally, the carbonyl-functional (co)polymer is selected from the group consisting of; carbon monoxide, acrolein, vinyl methyl ketone, vinyl ethyl ketone, vinyl isobutyl ketone, isopropenyl methyl ketone, vinyl phenyl ketone, diacetone (meth)acrylamide, acetonyl acrylate, acetoacetoxyethyl (meth)acrylate, and diacetone (meth)acrylate (co)polymers. An example of a carbon monoxide containing copolymer is ELVALOY™ 741, a terpolymer of ethylene/vinyl acetate/carbon monoxide.

The polymer may be a copolymer of the carbonyl-functional monomer units. In particular, the carbonyl functional polymer may further comprise ethylenically unsaturated hydrophilic monomer units, and/or hydrophobic monomer units. The copolymer, in some embodiments, may be a crosslinked copolymer. In particular, the carbonyl functional copolymer may further comprise comonomer units having more than one ethylenically unsaturated groups.

As used herein "hydrophilic monomers" are those polymerizable monomers having a water miscibility (water in monomer) of at least 1 wt. %, preferably at least 5 weight % without reaching a cloud point, and contain no functional groups that would interfere with the binding of biological substances to the ligand group. The copolymer may comprise 0 to 90 wt. % of such monomer units in the monomer solution. When present, the polymer generally comprises 1 to 90 wt. % of such of such monomer units based on 100 wt. % total monomer.

The hydrophilic groups of the hydrophilic monomers may be neutral, have a positive charge, a negative charge, or a combination thereof. With some suitable ionic monomers, the ionic group can be neutral or charged depending on the pH conditions. This class of monomers is typically used to impart a desired hydrophilicity, i.e. water solubility or dispersibility to the copolymer. These comonomers are typically used to impart a desired water solubility/dispersibility of the ligand functionalized copolymer. A negatively charged comonomer may be included as long as it is in small enough amounts that it doesn't interfere with the ligand binding interaction. In applications for viral capture, the addition of a hydrophilic monomer having a positive charge at the selected pH may allow selective binding and flocculation of viruses while repelling positively charged biological materials such as antibodies.

Some exemplary ionic monomers that are capable of providing a positive charge are amino (meth)acrylates or amino (meth)acrylamides of Formula IV or quaternary ammonium salts thereof. The counter ions of the quaternary ammonium salts are often halides, sulfates, phosphates, nitrates, and the like.

IV where X is —O— or —NR$^3$—;
R$^7$ is independently H or CH$_3$,
R$^6$ is a C$_2$ to C$_{10}$ alkylene, preferably C$_2$-C$_6$.
Each R$^8$ is independently hydrogen, alkyl, hydroxyalkyl (i.e. an alkyl substituted with a hydroxy), or aminoalkyl (i.e. an alkyl substituted with an amino). Alternatively, the two R$^8$ groups taken together with the nitrogen atom to which they are attached can form a heterocyclic group that is aromatic, partially unsaturated (i.e. unsaturated but not aromatic), or saturated, wherein the heterocyclic group can optionally be fused to a second ring that is aromatic (e.g. benzene), partially unsaturated (e.g. cyclohexene), or saturated (e.g. cyclohexane).

It will be understood with respect to Formula IV that the depicted (meth)acrylate group may be replaced by another ethylenically unsaturated group of reduced reactivity, such as methacrylate, (meth)acrylamide, vinyl, vinyloxy, allyl, allyloxy, and acetylenyl.

In some embodiments of Formula IV, both R$^8$ groups are hydrogen. In other embodiments, one R$^8$ group is hydrogen and the other is an alkyl having 1 to 10, 1 to 6, or 1 to 4 carbon atoms. In still other embodiments, at least one of R$^8$ groups is a hydroxy alkyl or an amino alkyl that have 1 to 10, 1 to 6, or 1 to 4 carbon atoms with the hydroxy or amino group being positioned on any of the carbon atoms of the alkyl group. In yet other embodiments, the R$^8$ groups combine with the nitrogen atom to which they are attached to form a heterocyclic group. The heterocyclic group includes at least one nitrogen atom and can contain other heteroatoms such as oxygen or sulfur. Exemplary heterocyclic groups include, but are not limited to imidazolyl. The heterocyclic group can be fused to an additional ring such as a benzene, cyclohexane, or cyclohexane. Exemplary heterocyclic groups fused to an additional ring include, but are not limited to, benzoimidazolyl.

Exemplary amino acrylates (i.e. X in Formula IV is oxy) include N,N-dialkylaminoalkyl (meth)acrylates such as, for example, N,N-dimethylaminoethyl(meth)acrylate, N,N-diethylaminoethylacrylate, N,N-diethylaminoethylacrylate, N,N-dimethylaminopropyl(meth)acrylate, N-tert-butylaminopropyl(meth)acrylate, and the like.

Exemplary amino (meth)acrylamides (i.e. X in Formula IV is —NR$^3$—) include, for example, N-(3-aminopropyl)methacrylamide, N-(3-aminopropyl)acrylamide, N-[3-(dimethylamino)propyl]methacrylamide, N-[3-(dimethylamino)propyl]acrylamide, N-(3-imidazolylpropyl)methacrylamide, N-(3-imidazolylpropyl)acrylamide, N-(2-imidazolylethyl)methacrylamide, N-(1,1-dimethyl-3-imidazolylpropyl)methacrylamide, N-(1,1-dimethyl-3-imidazolylpropyl)acrylamide, N-(3-benzimidazolylpropyl)acrylamide, and N-(3-benzimidazolylpropyl)methacrylamide.

Exemplary quaternary salts of the monomers of Formula IV include, but are not limited to, (meth)acrylamidoalkyltrimethylammonium salts (e.g. 3-methacrylamidopropyltrimethylammonium chloride and 3-acrylamidopropyltrimethylammonium chloride) and (meth)acryloxyalkyltrimethylammonium salts (e.g. 2-acryloxyethyltrimethylammonium chloride, 2-methacryloxyethyltrimethylammonium chloride, 3-methacryloxy-2-hydroxypropyltrimethylammonium chloride, 3-acryloxy-2-hydroxypropyltrimethylammonium chloride, and 2-acryloxyethyltrimethylammonium methyl sulfate).

Other monomers that can provide positively charged groups to the polymer include the dialkylaminoalkylamine adducts of alkenylazlactones (e.g. 2-(diethylamino)ethylamine, (2-aminoethyl)trimethylammonium chloride, and 3-(dimethylamino)propylamine adducts of vinyldimethylazlactone) and diallylamine monomers (e.g. diallylammonium chloride and diallyldimethylammonium chloride).

In some preferred embodiments, the second hydrophilic monomer may have an acrylate group, or other ethylenically unsaturated groups, and a poly(alkylene oxide) group; e.g. monoacrylated poly(alkylene oxide) compounds, where the terminus is a hydroxy group, or an alkyl ether group. Such monomers are of the general formula:

V, wherein each R$^3$ is independently H or C$_1$-C$_4$ alkyl, and n is at least 2.

In one embodiment, the poly(alkylene oxide) group (depicted as —(CH(R$^3$)—CH$_2$—O)$_n$—) is a poly(ethylene oxide) (co)polymer. In another embodiment, the poly(alkylene oxide) group is a poly(ethylene oxide-co-propylene oxide) copolymer. Such copolymers may be block copolymers, random copolymers, or gradient copolymers.

Other representative examples of suitable hydrophilic monomers include but are not limited to acrylic acid; methacrylic acid; 2-acrylamido-2-methyl-1-propanesulfonic acid; 2-hydroxyethyl (meth)acrylate; N-vinylpyrrolidone; N-vinylcaprolactam; acrylamide; mono- or di-N-alkyl substituted acrylamide; t-butyl acrylamide; dimethylacrylamide; N-octyl acrylamide; poly(alkoxyalkyl) (meth)acrylates including 2-(2-ethoxyethoxy)ethyl (meth)acrylate, 2-ethoxyethyl (meth)acrylate, 2-methoxyethoxyethyl (meth)acrylate, 2-methoxyethyl methacrylate, polyethylene glycol mono (meth)acrylates; alkyl vinyl ethers, including vinyl methyl ether; and mixtures thereof. Preferred hydrophilic monomers include those selected from the group consisting of dimethylacrylamide, 2-hydroxyethyl (meth)acrylate and N-vinylpyrrolidinone.

The copolymer may further comprise hydrophobic monomer units, in amounts that do not deleteriously affect the binding performance of the ligand polymer, and the water dispersibility thereof. When present, the polymer generally comprises 1 to 20 wt. % of such monomer units based on 100 wt. % total monomer.

Useful classes of hydrophobic monomers include alkyl acrylate esters and amides, exemplified by straight-chain, cyclic, and branched-chain isomers of alkyl esters containing $C_1$-$C_{30}$ alkyl groups and mono- or dialkyl acrylamides containing $C_1$-$C_{30}$ alkyl groups. Useful specific examples of alkyl acrylate esters include: methyl acrylate, ethyl acrylate, n-propyl acrylate, n-butyl acrylate, iso-amyl acrylate, n-hexyl acrylate, n-heptyl acrylate, isobornyl acrylate, n-octyl acrylate, iso-octyl acrylate, 2-ethylhexyl acrylate, iso-nonyl acrylate, decyl acrylate, undecyl acrylate, dodecyl acrylate, lauryl acrylate, tridecyl acrylate, and tetradecyl acrylate. Useful specific examples of alkyl acrylamides include mono- and diacrylamides having pentyl, hexyl, heptyl, isobornyl, octyl, 2-ethylhexyl, iso-nonyl, decyl, undecyl, dodecyl, tridecyl, and tetradecyl groups may be used. The corresponding methacrylate esters may be used.

Useful classes of hydrophobic monomers further include vinyl monomers such as vinyl acetate, styrenes, and alkyl vinyl ethers, maleic anhydride and polyfunctional monomers.

The ligand functional polymer may be prepared by condensation of the carbonyl functional (co)polymer with a ligand compound of Formula I:

I

Wherein
$R^2$ is a covalent bond, a $C_2$ to $C_{12}$ alkylene, a $C_5$-$C_{12}$ (hetero)arylene, $R^9$ is $C_2$ to $C_{12}$ alkylene or $C_5$-$C_{12}$ (hetero)arylene,
each $R^3$ is independently H, —OH, $C_1$-$C_{12}$ alkyl, or $C_5$-$C_{12}$ (hetero)aryl, preferably H or $C_1$-$C_4$ alkyl,
$R^4$ is H, $C_1$-$C_{12}$ alkyl, $C_5$-$C_{12}$ (hetero)aryl, or —N($R^3$)$_2$, preferably H, or $C_1$-$C_4$ alkyl.

The resulting polymer will have pendent guanidinyl groups of the formula:

wherein
$R^1$ is H, $C_1$-$C_{12}$ alkyl, or $C_5$-$C_{12}$ (hetero)aryl,
$R^2$ is a covalent bond, a $C_2$ to $C_{12}$ alkylene, a $C_5$-$C_{12}$ (hetero)arylene,

$R^9$ is $C_2$ to $C_{12}$ alkylene or $C_5$-$C_{12}$ (hetero)arylene,
each $R^3$ is independently H, —OH, $C_1$-$C_{12}$ alkyl, or $C_5$-$C_{12}$ (hetero)aryl, preferably H or $C_1$-$C_4$ alkyl,
$R^4$ is H, $C_1$-$C_{12}$ alkyl, $C_5$-$C_{12}$ (hetero)aryl, or —N($R^3$)$_2$, preferably H, or $C_1$-$C_4$ alkyl.

More particularly, the pendent ligand groups will be of the formula:

$R^9$ is $C_2$ to $C_{12}$ alkylene or $C_5$-$C_{12}$ (hetero)arylene,
each $R^3$ is independently H, —OH, $C_1$-$C_{12}$ alkyl, or $C_5$-$C_{12}$ (hetero)aryl, preferably H or $C_1$-$C_4$ alkyl,
$R^4$ is H, $C_1$-$C_{12}$ alkyl, $C_5$-$C_{12}$ (hetero)aryl, or —N($R^3$)$_2$, preferably H, or $C_1$-$C_4$ alkyl.

The reaction may be illustrated as follows:

where
-($M^{CO}$)$_w$- are carbonyl functional monomer units having "w" polymerized monomer units,
-($M^{Hydrophil}$)$_x$- are hydrophilic monomer units having "x" polymerized monomer units,
-($M^{hydrophob}$)$_z$- are hydrophobic monomer units having "z" polymerized monomer units
($M^{Lig}$)$_y$ are ligand functional monomer units having "y" polymerized monomer units,
where y is less than or equal to w; i.e. all or a portion of the carbonyl groups are functionalized by the ligand compound of Formula I. The w, x and z subscripts correspond to the weight ranges of the monomers used: w may comprise 10 to 100 wt. % of the monomer mixture, x may comprise 0 to 90 wt. % of the monomer mixture, and z may comprise 0 to 20 wt. % of the monomer mixture. "y" indicates the number of carbonyl functional groups functionalized with the ligand groups, and w* indicates the number of unfunctionalized carbonyl groups.

Alternatively to functionalizing the carbonyl functional polymer with a ligand compound of formula I, the ligand functional polymer may be prepared by polymerizing a monomer of the formula:

VI wherein
$R^1$ is H, $C_1$-$C_{12}$ alkyl, or $C_5$-$C_{12}$ (hetero)aryl,
$R^2$ is a covalent bond, a $C_2$ to $C_{12}$ alkylene, a $C_5$-$C_{12}$ (hetero)arylene, $R^9$ is $C_2$ to $C_{12}$ alkylene or $C_5$-$C_{12}$ (hetero)arylene,
each $R^3$ is independently H, —OH, $C_1$-$C_{12}$ alkyl, or $C_5$-$C_{12}$ (hetero)aryl, preferably H or $C_1$-$C_4$ alkyl,
$R^4$ is H, $C_1$-$C_{12}$ alkyl, $C_5$-$C_{12}$ (hetero)aryl, or —N($R^3$)$_2$, preferably H, or $C_1$-$C_4$ alkyl.
X is —O— or —NR$^3$—
$R^6$ is a $C_2$ to $C_{12}$ alkylene, and
$R^7$ is H or $CH_3$.

The monomer of Formula VI may be copolymerized with the hydrophilic monomers previously described.

Alternatively, the ligand functional polymer may be prepared by polymerizing a monomer of Formula VII. The monomer of Formula VII may be copolymerized with the hydrophilic monomers previously described.

VII wherein
$R^1$ is H, $C_1$-$C_{12}$ alkyl, or $C_5$-$C_{12}$ (hetero)aryl,
$R^2$ is a covalent bond, a $C_2$ to $C_{12}$ alkylene, a $C_5$-$C_{12}$ (hetero)arylene, $R^9$ is $C_2$ to $C_{12}$ alkylene or $C_5$-$C_{12}$ (hetero)arylene,
each $R^3$ is independently H, —OH, $C_1$-$C_{12}$ alkyl, or $C_5$-$C_{12}$ (hetero)aryl, preferably H or $C_1$-$C_4$ alkyl,
$R^4$ is H, $C_1$-$C_{12}$ alkyl, $C_5$-$C_{12}$ (hetero)aryl, or —N($R^3$)$_2$, preferably H, or $C_1$-$C_4$ alkyl, and $R^7$ is H or $CH_3$.

The disclosure further provides a functionalized substrate comprising a base substrate and a grafted or ungrafted coating of the ligand functional polymer thereon. Preferably the base substrate is a porous base substrate having interstitial and outer surfaces.

The base substrate may be formed from any suitable metallic, thermoplastic, or thermoset material. The material may be an organic or inorganic polymeric material. Suitable organic polymeric materials include, but are not limited to, poly (meth)acrylates, poly(meth)acrylamides, polyolefins, poly (isoprenes), poly(butadienes), fluorinated polymers, chlorinated polymers, polyamides, polyimides, polyethers, poly (ether sulfones), poly(sulfones), poly(vinyl acetates), copolymers of vinyl acetate, such as poly(ethylene)-co-poly (vinyl alcohol), poly(phosphazenes), poly(vinyl esters), poly (vinyl ethers), poly(vinyl alcohols), and poly(carbonates). Suitable inorganic polymeric materials include, but are not limited to, quartz, silica, glass, diatomaceous earth, and ceramic materials.

Suitable polyolefins include, but are not limited to, poly (ethylene), poly(propylene), poly(1-butene), copolymers of ethylene and propylene, alpha olefin copolymers (such as copolymers of ethylene or propylene with 1-butene, 1-hexene, 1-octene, and 1-decene), poly(ethylene-co-1-butene) and poly(ethylene-co-1-butene-co-1-hexene).

Suitable fluorinated polymers include, but are not limited to, poly(vinyl fluoride), poly(vinylidene fluoride), copolymers of vinylidene fluoride (such as poly(vinylidene fluoride-co-hexafluoropropylene), and copolymers of chlorotrifluoroethylene (such as poly(ethylene-co-chlorotrifluoroethylene).

Suitable polyamides include, but are not limited to, poly (iminoadipoyliminohexamethylene), poly(iminoadipoyliminodecamethylene), and polycaprolactam. Suitable polyimides include, but are not limited to, poly(pyromellitimide).

Suitable poly(ether sulfones) include, but are not limited to, poly(diphenylether sulfone) and poly(diphenylsulfone-co-diphenylene oxide sulfone).

Suitable copolymers of vinyl acetate include, but are not limited to, poly(ethylene-co-vinyl acetate) and such copolymers in which at least some of the acetate groups have been hydrolyzed to afford various poly(vinyl alcohols).

The base substrate may be in any form such as particles, fibers, films or sheets. Suitable particles include, but are not limited to, magnetic particles, organic particles, inorganic particles, and porous and nonporous particles. Preferably the base substrate is porous. Suitable porous base substrates include, but are not limited to, porous particles, porous membranes, porous nonwoven webs, and porous fibers.

In some embodiments, the porous base substrate is formed from propylene homo- or copolymers, most preferably propylene homopolymers. Polypropylene polymers are often a material of choice for porous articles, such as nonwovens and microporous films, due to properties such as non-toxicity, inertness, low cost, and the ease with which it can be extruded, molded, and formed into articles.

In many embodiments, the porous base substrate has an average pore size that is typically greater than about 0.2 micrometers in order to minimize size exclusion separations, minimize diffusion constraints and maximize surface area and separation based on binding of a target molecule. Generally, the pore size is in the range of 0.1 to 10 micrometers, preferably 0.5 to 3 micrometers and most preferably 0.8 to 2 micrometers when used for binding of viruses. The efficiency of binding other target molecules may confer different optimal ranges.

Suitable porous base substrates include, but are not limited to, porous and microporous membranes, particles, nonwoven webs, and fibers. In some embodiments, the porous base substrate is a microporous membrane such as a thermally-induced phase separation (TIPS) membrane. TIPS membranes are often prepared by forming a homogenous solution of a thermoplastic material and a second material above the melting point of the thermoplastic material. Upon cooling, the thermoplastic material crystallizes and phase separates from the second material. The crystallized thermoplastic material is often stretched. The second material is optionally removed either before or after stretching. Microporous membrane are further disclosed in U.S. Pat. Nos. 4,539,256 (Shipman), 4,726,989 (Mrozinski), 4,867,881 (Kinzer), 5,120,594

(Mrozinski), 5,260,360 (Mrozinski et al.), and 5,962,544 (Waller), all of which are assigned to 3M Company (St. Paul, Minn.). Further, the microporous film can be prepared from ethylene-vinyl alcohol copolymers as described in U.S. Pat. No. 5,962,544 (Waller).

Some exemplary TIPS membranes comprise poly(vinylidene fluoride) (PVDF), polyolefins such as polyethylene homo- or copolymers or polypropylene homo- or copolymers, vinyl-containing polymers or copolymers such as ethylene-vinyl alcohol copolymers and butadiene-containing polymers or copolymers, and acrylate-containing polymers or copolymers. For some applications, a TIPS membrane comprising PVDF is particularly desirable. TIPS membranes comprising PVDF are further described in U.S. Pat. No. 7,338,692 (Smith et al.).

In another exemplary embodiment the porous bases substrate comprises a nylon microporous film or sheet, such as those described in U.S. Pat. Nos. 6,056,529 (Meyering et al.), 6,267,916 (Meyering et al.), 6,413,070 (Meyering et al.), 6,776,940 (Meyering et al.), 3,876,738 (Marinacchio et al.), 3,928,517, 4,707,265 (Knight et al.), and 5,458,782 (Hou et al.).

In other embodiments, the porous base substrate is a nonwoven web which may include nonwoven webs manufactured by any of the commonly known processes for producing nonwoven webs. As used herein, the term "nonwoven web" refers to a fabric that has a structure of individual fibers or filaments which are randomly and/or unidirectionally interlaid in a mat-like fashion.

For example, the fibrous nonwoven web can be made by wet laid, carded, air laid, spunlaced, spunbonding or meltblowing techniques or combinations thereof. Spunbonded fibers are typically small diameter fibers that are formed by extruding molten thermoplastic polymer as filaments from a plurality of fine, usually circular capillaries of a spinneret with the diameter of the extruded fibers being rapidly reduced. Meltblown fibers are typically formed by extruding the molten thermoplastic material through a plurality of fine, usually circular, die capillaries as molten threads or filaments into a high velocity, usually heated gas (e.g. air) stream which attenuates the filaments of molten thermoplastic material to reduce their diameter. Thereafter, the meltblown fibers are carried by the high velocity gas stream and are deposited on a collecting surface to from a web of randomly disbursed meltblown fibers. Any of the non-woven webs may be made from a single type of fiber or two or more fibers that differ in the type of thermoplastic polymer and/or thickness.

Further details on the manufacturing method of non-woven webs of this invention may be found in Wente, Superfine Thermoplastic Fibers, 48 INDUS. ENG. CHEM. 1342 (1956), or in Wente et al., Manufacture Of Superfine Organic Fibers, (Naval Research Laboratories Report No. 4364, 1954).

In one embodiment the base substrate may have a coating of the ligand functional (co)polymer on a surface thereon. Useful coating techniques include applying a solution or dispersion of the (co)polymer, optionally including a crosslinker, onto the base substrate. Polymer application is generally followed by evaporating the solvent to form the polymer coating. Coating methods include the techniques commonly known as dip, spray, knife, bar, slot, slide, die, roll, or gravure coating. Coating quality generally depends on mixture uniformity, the quality of the deposited liquid layer, and the process used to dry or cure the liquid layer.

In some embodiments, the carbonyl functional (co)polymer is first coated on the base substrate and subsequently reacted with the ligand compound of Formula I. Useful crosslinkers for the coating operation in these instances include carbonyl reactive compounds such as polyamines, polyhydrazines, and polyhydrazides.

In other embodiments, the ligand functional (co)polymer itself is coated on the base substrate. Useful crosslinkers in these instances include amine reactive compounds such as bis- and polyepoxides, polycarboxylic acids and their derivatives (e.g., acid chlorides), polyisocyanates, and formaldehyde-based crosslinkers such as hydroxymethyl and alkoxymethyl functional crosslinkers, such as those derived from urea or melamine.

In other embodiments, the ligand functional copolymer is coated on the base substrate by polyelectrolyte layer-by-layer coating techniques, such as those described in EP 472,990.

In another embodiment, the ligand-functional polymer may be grafted to the surface of the base substrate; i.e. a covalent bond is formed between the ligand functional polymer and the polymer base substrate. The covalent bond may be formed by displacement, condensation or free radical methods. The nature of the grafting depends on the type of polymer used for the base substrate.

In some embodiments, the base polymer has carbonyl-reactive functional groups, such as amines on the surface thereof. These surface functional groups may react with extant carbonyl functional groups on the ligand functional polymer. In another embodiment, the surface of the substrate may be provided with amine-reactive functional groups, such as halide, epoxy, ester, isocyanate groups, that can react with the guanidino groups of the ligand functionalized polymer.

In some embodiments the polymer may be grafted to the surface of a substrate by ionizing radiation-initiated graft polymerization of a monomer such as those of Formulas VI or VII, optionally with other hydrophilic or hydrophobic monomers previously described. Alternatively, a carbonyl functional monomer may be grafted to the surface of a substrate by ionizing radiation-initiated graft polymerization, followed by functionalization by reaction with a ligand compound of Formula I.

In some embodiments, the surface of the substrate may be free radically functionalized with a grafting monomer having a free-radically polymerizable group and a second functional group reactive with the ligand functional polymer. Such monomers may include isocyanatoethyl (meth)acrylate or glycidyl (meth)acrylate.

The grafting monomers can graft (i.e. forming a covalent bond) to the surface of the base substrate when exposed to an ionizing radiation preferably e-beam or gamma radiation. That is, reaction of (meth)acryloyl groups of the grafting monomers with the surface of the porous base substrate in the presence of the ionizing radiation results in the reaction of ethylenically unsaturated free-radically polymerizable groups being directly grafted to the base substrate via the acrylate group, and further provides the surface of the substrate with a reactive functional groups that may be subsequently reacted with the ligand functional polymer.

The methods of the present disclosure involve the irradiation of porous or non-porous substrate surfaces with ionizing radiation to prepare free radical reaction sites on such surfaces upon which the functional monomers are grafted. The functional groups of the functional monomers then allow the ligand functional polymer to be grafted to the surface of the substrate. "Ionizing radiation" means radiation of a sufficient dosage and energy to cause the formation of free radical reaction sites on the surface(s) of the base substrate. Ionizing radiation may include beta, gamma, electron-beam, x-ray and other electromagnetic radiation. In some instances, corona radiation can be sufficiently high energy radiation. The radiation is sufficiently high energy, that when absorbed by the surfaces of the base substrate, sufficient energy is transferred to that support to result in the cleavage of chemical bonds in that support and the resultant formation of a free radical site on the support.

The method of grafting (or coating) a ligand functionalized polymer to the surface of the substrate alters the original nature of the base substrate, as the substrate bears a grafted or ungrafted coating of the ligand functional polymer. The present invention enables the formation of ligand functionalized polymer substrates having many of the advantages of a base substrate (e.g., mechanical and thermal stability, porosity), but with enhanced affinity for biological species such as viruses, resulting from the monomers and steps used to form a given functionalized substrate.

The porous substrates having a coating of ligand-functionalized polymer are particularly suited as filter media, for the selective binding and removal of contaminating proteins, cells, cell debris, microbes, nucleic acids, and/or viruses from biological samples. The present disclosure further provides a method for the removal of target biological species from a biological sample by contacting the sample with the ligand polymer functionalized substrate as described herein.

The ligand functionalized (co)polymer (either the polymer per se, or a substrate having a coating thereof) is useful for the purification of biological or other fluid samples comprising biologically derived species (biological species). Biological species include, but are not limited to, cells, cell debris, proteins, nucleic acids, endotoxins, and viruses. Cells and cell debris include those derived from archaea, bacteria, and eucaryota. Bacteria include, but are not limited to, Gram-negatives such as *Pseudomonas* species, *Escherichia coli*, *Helicobacter pylori*, and *Serratia marcesens*; Gram-positives such as *Staphylococcus* species, *Enterococcus* species, *Clostridium* species, *Bacillus* species, and *Lactobacillus* species; bacteria that do not stain traditionally by Gram's method such as *Mycobacterium* species, and non-vegetative forms of bacteria such as spores. Eucaryota include, but are not limited to, animal cells, algae, hybridoma cells, stem cells, cancer cells, plant cells, fungal hyphae, fungal spores, yeast cells, parasites, parasitic oocysts, insect cells, and helminthes. Proteins, include, but are not limited to, natural proteins, recombinant proteins, enzymes, and host cell proteins. Viruses include, but are not limited to, enveloped species such as Herpesviruses, Poxviruses, Adenoviruses, Papovaviruses, Coronaviruses, retroviruses such as HIV, and Plasmaviridae; and non-enveloped species such as Caliciviridae, Corticoviridae, Myoviridae, and Picornaviridae.

In some embodiments, the biological species being removed from the fluid is the object of the purification. For example, a recombinant protein or enzyme may be prepared in cell culture, the (co)polymer can be added to flocculate the protein or enzyme, and the precipitate can be separated as the first step in the purification process for the protein or enzyme. In another example, the (co)polymer or a substrate with a coating thereof, may be used to capture microorganisms from a fluid as the first step in a process of concentrating, enumerating, and/or identifying the microorganisms.

In other embodiments, the biological species being removed from the fluid is a contaminant that must be removed prior to additional processing steps for the fluid. The polymer can be used as a flocculant to facilitate the removal of cells and cell debris from a cell culture or fermentation broth prior to, subsequent to, or in place of a centrifuge or depth filtration operation. For example, the (co)polymer can be used to flocculate cells in a cell culture broth prior to centrifugation, and thereby improve the efficiency with which the centrifugation process separates the cell mass from the liquid centrate. Alternatively, it can be added to the liquid centrate after a centrifugation step to flocculate suspended cell debris and dissolved host cell proteins and nucleic acids, thereby increasing the efficiency of a subsequent depth filtration step. It can be used to flocculate or precipitate suspended bacteria, viruses, or other microorganisms. It can be used to precipitate either desired or contaminating proteins or nucleic acids from solution. Significantly, the ligand functional (co)polymers, or substrates having a coating thereof, are useful under conditions of high salt concentration or high ionic strength, i.e., they are "salt tolerant". The term "salt" is meant to include all low molecular weight ionic species which contribute to the conductivity of the solution. The importance of utility of the ligand functional (co)polymers in the presence of salt is that many process solutions used in biopharmaceutical or enzyme manufacture have conductivities in the range of 15-30 mS/cm (approximately 150-300 mM salt) or more. Salt tolerance can be measured in comparison to that of the conventional quaternary amine or Q ligand (e.g. trimethylammonium ligand), whose primarily electrostatic interactions with many biological species rapidly deteriorates at conductivities three- to six-fold less than the target range. For example, membranes derivatized with the conventional Q ligand exhibit a drop in $\phi$X174 viral clearance from a six log-reduction value (LRV) to a one (1) LRV in going from 0 to 50 mM NaCl (ca. 5-6 mS/cm conductivity). Viruses such as $\phi$X174 which have pIs close to 7 (are neutral or near-neutral) are extremely difficult to remove from process streams. Similar problems are observed when attempting to remove other biological species from process fluids. For example, when attempting to remove positively charged proteins such as host cell proteins through the use of filtration devices functionalized with conventional Q ligands, the process fluid may have to be diluted two-fold or more in order to reduce the conductivity to an acceptable range. This is expensive and dramatically increases the overall processing time.

When used as a flocculant, the amount of ligand functional (co)polymer that is added relative to the amount of sample can vary over a wide range. Generally, the amount added will produce a final concentration of (co)polymer in the mixture of from about 0.01 micrograms/mL to about 5000 micrograms/mL. The optimal amount of (co)polymer added will depend upon the concentration of the species one desires to flocculate. Typically, the amount of polymer relative to the amount of species being flocculated will be in the range of 0.01% to 100% by weight, preferably 0.05%-30% by weight, more preferably about 0.1%-10% by weight. The optimal amount is readily assessed by challenging the sample with a series of polymer concentrations as is well known in the art. While the above concentration ranges are typical, one skilled in the art will realize that other ranges may work in some instances. Flocculation efficiency also depends upon the physical and chemical characteristics of the species being flocculated. For example, we have found that optimal flocculation of the near neutral virus $\phi$X174 from aqueous suspension occurs at a polymer to virus weight ratio of about 800-1000%.

The biological sample is contacted with the ligand functionalized polymer (either the polymer per se, or a substrate having a coating thereof) for a time sufficient to interact and form a complex with the target biological species disposed (dissolved or suspended) in the solution when the solution comprises from 0 to about 50 mM salt, preferably when the solution comprises from 0 to about 150 mM salt, more preferably when the solution comprises from 0 to about 300 mM salt or higher, such that the concentration of the target biological species remaining disposed in the solution is less than 50% of its original concentration. It is more preferred that the solution is contacted with the ligand functionalized polymer for a time sufficient to interact and form a complex with the target biological species disposed in the solution when the solution comprises from 0 to about 50 mM salt, preferably when the solution comprises from 0 to about 150 mM salt, more preferably when the solution comprises from 0 to about 300 mM salt or higher, such that the concentration of the target biological species remaining disposed in the solution is less than 10% of its original concentration. It is still more preferred that the solution is contacted with the ligand functionalized polymer for a time sufficient to interact and form a complex with the target biological species disposed in the solution when the solution comprises from 0 to about 50 mM salt, preferably when the solution comprises from 0 to about 150 mM salt, more preferably when the solution comprises from 0 to about 300 mM salt or higher, such that the concentration of the target biological species remaining disposed in the solution is less than 1% of its original concentration.

In many embodiments the ligand functionalized (co)polymer, being positively charged in aqueous media, will bind near neutral or negatively charged species to the ligand functional group of Formula II while other species (e.g., positively charged proteins such as monoclonal antibodies) will be excluded or repelled from the ligand functionalized substrate. In addition, as previously described, the substrate may be directly or indirectly grafted with one or more ionic monomers. In particular, the ligand functionalized polymer may comprise grafted ionic groups that are positively charged at the selected pH of the biological sample solution to enhance electrostatic charge repulsion of proteins, such as monoclonal antibodies, many of which are charged positive at neutral pH, and ligand functional groups of Formula II to provide salt tolerance.

In some embodiments the ligand functionalized polymer and coated substrate containing the bound biological species are disposable. In such embodiments, the binding of the biological species to the ligand functionalized polymer is preferably essentially irreversible because there is no need to recover the bound biological species. Nonetheless, if desired, one can reverse the binding of biological species by increasing the ionic strength or changing the pH of an eluting solution.

The substrate, having a grafted or ungrafted coating of the ligand functionalized polymer may be any previously described, but is preferably a microporous membrane. The membrane pore size desired is from 0.1 to 10 µm, preferably 0.5 to 3 micrometers and most preferably 0.8 to 2 micrometers. A membrane with a high surface area for the internal pore structure is desired, which typically corresponds to fine pore sizes. However, if the pore size is too small, then the membrane tends to plug with fine particulates present in the sample solution.

If desired, efficiency of binding and capture may be improved by using a plurality of stacked, ligand functionalized polymer coated porous membranes as a filter element. Thus the present disclosure provides a filter element comprising one or more layers of the porous, ligand functionalized polymer coated substrate. The individual layers may be the same or different, and may have layers of different porosity, and degree of grafting by the aforementioned grafting monomers. The filter element may further comprise an upstream prefilter layer and downstream support layer. The individual filter elements may be planar or pleated as desired.

Examples of suitable prefilter and support layer materials include any suitable porous membranes of polypropylene, polyester, polyamide, resin-bonded or binder-free fibers (e.g., glass fibers), and other synthetics (woven and non-woven fleece structures); sintered materials such as polyolefins, metals, and ceramics; yarns; special filter papers (e.g., mixtures of fibers, cellulose, polyolefins, and binders); polymer membranes; and others.

In another embodiment, there is provided a filter cartridge including the above-described filter element. In yet another embodiment, there is provided a filter assembly comprising the filter elements and a filter housing. In a further embodiment, this invention relates to a method of capture or removal of a target biological species comprising the steps of:

a) providing the filter element comprising one of more layers of the ligand functionalized base substrate of this disclosure, and b) allowing a moving biological solution containing a target biological species to impinge upon the upstream surface of the filter element for a time sufficient to effect binding of a target biological species.

The present invention is described above and further illustrated below by way of examples, which are not to be construed in any way as imposing limitations upon the scope of the invention. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

EXAMPLES

Examples 1-5

Diacetone acrylamide (40 grams), ethanol (60 grams) and VAZO 67 (0.2 gram) were charged to an 8 ounce glass bottle. The mixture was purged with a slow stream of nitrogen gas for 5 minutes, sealed, and then tumbled in a water bath equilibrated to 55° C. for 24 hours to convert the monomer to polymer. A portion of this polymer solution (4.07 grams) was diluted with methanol (16.48 grams) and mixed with aminoguanidine hydrochloride (1.08 grams, TCI America, Portland, Oreg.). Trifluoroacetic acid (4 drops) was added as catalyst, and the solution was mixed for 2 hours at ambient temperature. IR and $^1$H-NMR analyses confirmed the formation of poly(diacetoneacrylamide guanylhydrazone) (polymer 1).

By similar procedures, polymers 2-5 were prepared by converting 20, 40, 60, and 80% of the repeat units to guanylhydrazone functionality.

Examples 6-10

Copolymers of dimethylacrylamide and diacetoneacrylamide were prepared in methanol solution by the procedure described in Example 1. The copolymers, containing 20, 40, 60, 80 and 0% by weight dimethylacrylamide, were reacted with aminoguanidine by the procedure described in Example 1 except that concentrated hydrochloric acid was used as catalyst instead of trifluoroacetic acid, to produce the corresponding guanylhydrazone copolymers 6-10.

Example 11

Figure 1:
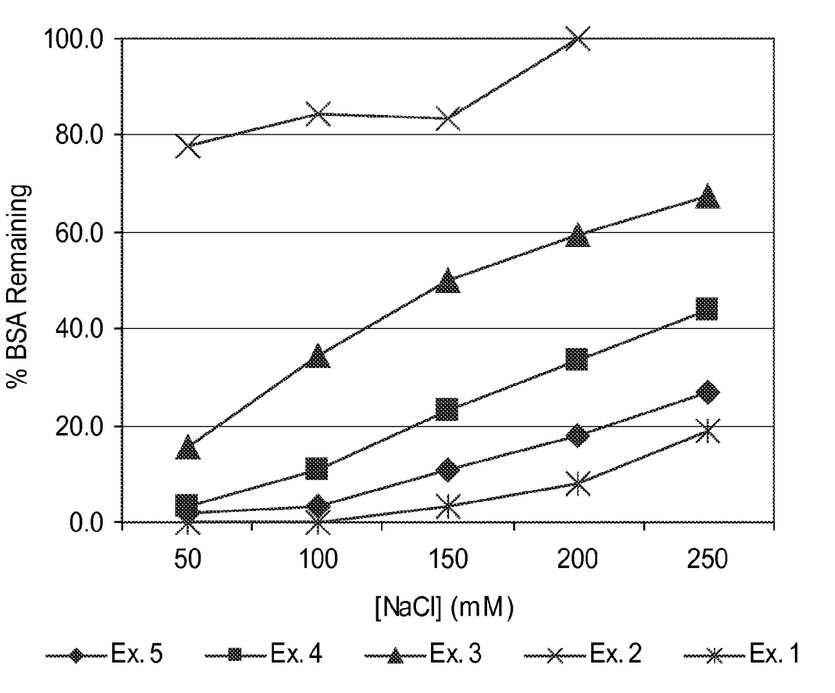
FIG. 1 is a plot of the bovine serum albumin precipitation data of Example 1-5.

Guanylhydrazone polymers 1-5 were assayed for BSA precipitation according to the following procedure. Results are shown in FIG. 1.

A solution of bovine serum albumin (BSA, Sigma-Aldrich) was prepared in 10 mM MOPS buffer (4-morpholinepropanesulfonic acid), pH 7.5, and determined to have a concentration of BSA of 4.0 mg/mL. A series of BSA solutions were prepared containing various concentrations of sodium chloride according to the following Table 1:

TABLE 1

| [NaCl] (mM, final) | BSA solution (mL) | 5M NaCl (μL) | MOPS buffer (μL) |
| --- | --- | --- | --- |
| 0 | 10 | 0 | 500 |
| 50 | 10 | 100 | 400 |
| 100 | 10 | 200 | 300 |
| 150 | 10 | 300 | 200 |
| 200 | 10 | 400 | 100 |
| 250 | 10 | 500 | 0 |

Solutions of the polymers from Examples 1-5 were diluted with deionized water to 1% solids by weight and adjusted to pH 7.

A 5 mL polypropylene centrifuge tube was charged with 2.0 mL of BSA solution, followed by 125 μL of diluted polymer solution. The centrifuge tube was sealed and tumbled end over end for 30 minutes, then centrifuged at 2000 rcf for 10 minutes. A BSA standard solution was prepared by mixing 2 mL of original BSA solution with 125 μL of MOPS buffer. A serial 1:1 dilution was performed to provide a total of 7 BSA standards. These seven standards were pipetted (200 μL) in triplicate into wells of a 96-well microtiter plate, along with triplicate samples of the supernates from each polymeric flocculant being evaluated. Three wells containing DI water as a blank were also included. The plate was analyzed using a SpectraMAX 250 Microplate Spectrophotometer System (Molecular Devices Corp, Sunnyvale, Calif.) using a wavelength of 293 nm. Comparison of the absorptions of the flocculant solutions to those of the standards provided a measure of the percentage of BSA precipitated.

Comparative Example 1

Poly(Methacrylamidopropyltrimethylammonium Chloride) (pMAPTAC)

MAPTAC (160 grams of a 50% by weight solution in water, from Aldrich, Milwaukee, Wis.), ethanol (40 grams) and sodium persulfate (0.4 gram) were charged to a 16 ounce glass bottle. The mixture was purged with a slow stream of nitrogen gas for 10 minutes, sealed, and then tumbled in a water bath equilibrated to 55° C. for 24 hours to convert the monomer to polymer. This polymer solution was diluted with deionized water (80 grams) and ethanol (40 grams) and mixed well. A sample for evaluation as a flocculant was prepared by dilution of a portion of this polymer to 1% solids by weight with deionized water, pH 7. A BSA precipitation test was conducted as described in Example 11, and the pMAPTAC was found to be a good flocculator at 0 mM NaCl, but it left 42%, 73%, and 100% of the BSA in solution at 50 mM, 100 mM, and 150 mM NaCl, respectively.

Example 12

Virus Flocculation

Aqueous suspensions of φX174 bacteriophage (ca. $10^9$ pfu/mL) were prepared in 10 mM TRIS((hydroxymethyl)aminomethane) pH 8.0 containing 0, 50 mM, and 150 mM NaCl. Aqueous solutions of flocculator polymers were prepared in DI water, pH 7, at 0.001% polymer by weight. 16 μL of polymer solution were added to a 2 mL sample of bacteriophage suspension in a centrifuge tube. The tube was sealed, vortexed, and rotated end-over-end for 2 hours. The tubes were then centrifuged at 3000 rcf for 10 minutes, and the resultant suspensions were filtered through a 0.45 micron sterile syringe filter (GHP Acrodisc, Pall Life Sciences). A 10-fold dilution series was prepared.

One mL of each dilution was mixed with 1 mL *E. coli* culture (grown to an optical density of 0.3-0.6 when measured at 550 nm). After waiting 5 minutes, a sterile pipet was used to mix 4.5 mL TSA Top agar with the dilution/*E. coli* mixture and plated on TSB plates. After the top agar had solidified, the plates were inverted and placed in a 37° C. incubator overnight. Plates were then removed from the incubator and φX174 plaques were counted and recorded. A dilution series of the original virus suspension was also evaluated in a similar manner. Comparison of the results allowed estimation of the LRV (log reduction in viral load) as a result of the flocculant treatment. Results for several polymers are listed in the following Table 2:

TABLE 2

| Polymer | φX174 LRV |
| --- | --- |
| Example 1 (0 NaCl) | 4.9 |
| Example 1 (50 mM NaCl) | 2.5 |
| Example 1 (150 mM NaCl) | 2.9 |
| Comparative Example 1 (0 NaCl) | 6.3 |
| Comparative Example 1 (50 mM NaCl) | 0.1 |
| Comparative Example 1 (150 mM NaCl) | 0.5 |

Example 13

Poly(vinylmethylketone) (1.0 gram, from Scientific Polymer Products, Ontario, New York) was dissolved in 4 grams of ethyl acetate. To this solution was added methanol (5 grams), aminoguanidine hydrochloride (1.58 grams), and concentrated hydrochloric acid (1 drop). The mixture was mixed for 1 hour, followed by the addition of methanol (5 grams) and deionized water (5 grams) to produce an orange-colored solution. Infrared and NMR analysis confirmed the conversion to the guanylhydrazone polymer. The polymer was diluted to 1% solids by weight with deionized water, pH 7. for evaluation as a BSA precipitant. This polymer showed >50% BSA precipitation up to 250 mM NaCl concentration.

Comparative Example 2

Poly(diallyldimethylammonium chloride) (pDADMAC)

To a 1 liter, 3-necked round bottom flask equipped with an overhead stirrer, condenser, heating mantle, thermocouple, and nitrogen inlet was charged DADMAC (105.6 grams of a 65% solids aqueous solution, from Aldrich, Milwaukee, Wis.), tetrasodium ethylenediaminetetraacetic acid (6 μL of a 20% solution by weight in deionized water), deionized water (121.8 grams), and 2,2'-azobis(2-amidinopropane) dihydrochloride (1.74 grams). Stirring was begun and the mixture purged with a slow stream of nitrogen gas for 15 minutes. The temperature of the stirring mixture was then slowly raised to 60° C. over one hour, then maintained at that temperature for an additional 24 hours. NMR analysis confirmed the formation of the expected polymer.

Examples 14-16

Copolymers of DADMAC with diacetoneacrylamide by procedures similar to that described in Comparative Example 2. The copolymers, containing 20, 40, and 80% by weight diacetoneacrylamide, were reacted with aminoguanidine by the procedure described in Example 1, to produce the corresponding 20, 40, and 80% guanylhydrazone copolymers 14-16, respectively. Solutions of these copolymers and of pDADMAC were prepared at 1% by weight in deionized water (pH 7) and evaluated in the BSA precipitation test. These flocculants displayed 0%, 30%, 62%, and 92% BSA precipitation at 100 mM NaCl for Comparative Example 2, Ex. 14, Ex. 15, and Ex. 16, respectively.

Example 17

A *Geobacillus stearothermophilus* purified spore suspension was provided by 3M consisting of approximately 1.4% by weight cell debris and spores. Test samples of broth containing 0, 100, 200, and 300 mM NaCl were prepared by a procedure similar to that described in Example 11. Solutions of polymers were prepared at 1.0% solids in DI water, pH 7, from the modified polymers of Examples 1, 6, and 8. A 1:4 dilution series of each of these polymers was prepared to provide a total of 6 polymer concentrations. Then 2 mL of broth sample was mixed with 0.5 mL of polymer solution, and the mixture was tumbled for 30 minutes, then centrifuged at 200 rcf for 5 minutes. Standards were prepared by mixing 2 mL of broth with 0.5 mL of DI water, carrying the mixture through the same mixing/centrifugation procedure, then preparing a 2-fold serial dilution (6 samples) from the supernate. Supernatants from the test solutions and from the standards were pipetted into a 96-well microtitration plate and assayed by absorbance measurement at 650 nm. Comparison of the absorptions of the flocculant solutions to those of the standards provided a measure of the flocculation efficiencies. Results are presented in the following Table 3:

Examples 18-20 and Comparative Examples 3-4

A 20:80 w/w copolymer of N,N-dimethylaminopropylacrylamide (DMAPAm) and diacetoneacrylamide (Comparative Example 3) was prepared in methanol solution by the procedure described in Example 1.

A sample of this polymer solution was diluted to 20% solids by adding more methanol, and enough butyl bromide was added to alkylate 50% of the DMAPAm units of the copolymer (Comparative Example 4).

Samples of Comparative Example 3 polymer solution were reacted with aminoguanidine hydrochloride by a procedure similar to that of Example 6 to produce copolymers in which 50% and 100% of the diacetoneacrylamide units were converted to guanylhydrazone units, respectively (Examples 18 and 19).

A sample of Comparative Example 4 was reacted with aminoguanidine hydrochloride by a procedure similar to that of Example 6 to convert all of the diacetoneacrylamide units to guanylhydrazone units (Example 20).

Samples of each of the above examples were diluted to 1% solids with deionized water, adjusted to pH 7, and evaluated for BSA precipitation (Table 4)

TABLE 4

| [NaCl] | % BSA Precipitated | | | |
|---|---|---|---|---|
| (mM) | Comp. 3 | Comp. 4 | Ex. 18 | Ex. 19 | Ex. 20 |
| 50 | 0 | 0 | 62 | 89 | 93 |
| 150 | 0 | 0 | 28 | 47 | 86 |
| 250 | 0 | 1 | 14 | 18 | 75 |

Similar copolymers were prepared by alkylation with dimethylsulfate, benzyl bromide and dodecylbromide, respectively, followed by conversion of the keto groups to guanylhydrazones. When tested for BSA precipitation, a synergistic effect was again observed for alkylation plus guanylation.

Example 21

A 50:50 w/w copolymer of DADMAC with diacetoneacrylamide was prepared by a procedure similar to that described in Comparative Example 2. A solution of this copolymer in

TABLE 3

| | | | % Turbidity Removed | | | |
|---|---|---|---|---|---|---|
| Polymer | (w/v %) | (µg/ml) | 0 mM NaCl | 100 mM NaCl | 200 mM NaCl | 300 mM NaCl |
| Example 1 | 0.2 | 2000 | 54.7 | 95.9 | 98.9 | 98.7 |
| " | 0.05 | 500 | 99.5 | 97.8 | 98.1 | 98.6 |
| " | 0.0125 | 125 | 95.7 | 97.0 | 95.0 | 92.1 |
| " | 0.003125 | 31.25 | 82.2 | 83.9 | 81.5 | 78.6 |
| " | 0.000781 | 7.81 | 76.6 | 73.5 | 71.5 | 68.0 |
| " | 0.000195 | 1.95 | 34 | 22.4 | 17.9 | 15.3 |
| Example 6 | 0.2 | 2000 | 0.0 | 0.0 | 0.0 | 0.0 |
| " | 0.05 | 500 | 101.3 | 45.5 | 21.9 | 24.8 |
| " | 0.0125 | 125 | 96.8 | 97.7 | 97.8 | 98.5 |
| " | 0.003125 | 31.25 | 83.5 | 82.1 | 81.6 | 78.5 |
| " | 0.000781 | 7.81 | 70.9 | 76.5 | 66.4 | 52.2 |
| " | 0.000195 | 1.95 | 25.8 | 28 | 24.4 | 17.5 |
| Example 8 | 0.2 | 2000 | 0.0 | 0.0 | 0.0 | 0.0 |
| " | 0.05 | 500 | 53.4 | 42.2 | 9.8 | 10.5 |
| " | 0.0125 | 125 | 90.0 | 74.2 | 14.6 | 37.9 |
| " | 0.003125 | 31.25 | 98.6 | 88.5 | 58.7 | 55.1 |
| " | 0.000781 | 7.81 | 80.0 | 75.1 | 67.7 | 56.3 |
| " | 0.000195 | 1.95 | 70.4 | 68.2 | 64.5 | 40.8 | methanol (1.32 grams of 30% solids solution) was diluted to 2% solids with deionized water, mixed with diaminoguanidine hydrochloride (74 milligrams) and concentrated hydrochloric acid (1 drop), and allowed to react at room temperature overnight to form the bis-guanylhydrazone copolymer. The solution was adjusted to pH 7 and diluted to 1% solids with DI water. This polymer exhibited good flocculation of BSA in solutions containing up to 250 mM sodium chloride.

Example 22

Diacetoneacrylamide (33.8 grams), methanol (400 mL), and aminoguanidine hydrochloride (22.1 grams) were placed in a 1 L round bottom flask and stirred magnetically until a homogeneous solution had formed. Trifluoroacetic acid (0.5 mL) was added and the mixture was stirred overnight at ambient temperature. The reaction mixture was concentrated on a rotary evaporator to produce a light yellow oil which crystallized on standing. Diethyl ether (250 mL) was added and the crystalline mass was broken up, filtered, washed with additional ether, and dried under vacuum for 3 hours to give the corresponding guanylhydrazone hydrochloride monomer (53.5 grams, 95.7% yield). This monomer (10 grams) was mixed with deionized water (23 grams), methanol (7 grams), and 2,2'-azobis(2-imidazolin-2-yl)propane (0.2 grams, from WAKO, Osaka, Japan). The mixture was purged with nitrogen gas for 15 minutes, then polymerized at 60° C. for 24 hours as described in Example 1. This polymer displayed flocculation properties identical to those of Example 1.

Example 23

A polypropylene spunbond/melt blown/spunbond (SMS) nonwoven (50 gsm basis weight) was coated with the polymer of Example 1 in a layer-by-layer process. Three coating baths were prepared:
Coating Bath #1: 1% wt/wt polyethylenimine (70,000 $M_n$) in isopropyl alcohol;
Coating Bath #2: 0.5% wt/wt poly(2-acrylamido-2-methyl-1-propanesulfonic acid, sodium salt) in deionized water;
Coating Bath #3: 1% wt/wt polymer of Example 1 in deionized water.

The following coating sequence was conducted (5 minute residence time in each bath) with a 5 minute rinse with deionized water after each coating layer was applied: #1, #2, #1, #2, #3, #2, #3, #2, and #3. After drying at room temperature overnight, a 16 mm diameter disk was cut from the coated web. This disk was placed in a 5 mL centrifuge tube, 2 mL of a *Clostridium sporogenes* spore suspension (with and without added sodium chloride) was added, and the mixture tumbled at room temperature for 30 minutes. The UV absorbance of the supernatant solution was measured at 640 nm and compared to the absorbance prior to contact with the disk, and indicated 46% and 58% removal of spores at 0 and 250 mM sodium chloride concentrations, respectively.

Example 24

Aminosilane coated glass microscope slides (obtained from Newcomer Supply, Middleton, Wis.) were dip coated, in sequence, with coating solution #2 from Example 23, rinsed with deionized water, coating solution #3 from Example 23, rinsed with deionized water, and dried at room temperature. The coated slides could then be used to capture bacteria or spores from aqueous media for enumeration or for identification. A control aminosilane slide coated with only coating solution #2 was found to bind almost no bacteria or spores.

Examples 25-28

A diacetoneacrylamide solution was prepared at 10% by weight in isopropanol. Several sheet substrates (ca. 4 inches by 6 inches), both membrane and non-woven, as listed in the table below, were placed in polyethylene bags (Ziploc™, S C Johnson, Racine, Wis.). Using a disposable pipette, the substrates were completely wetted with the diacetoneacrylamide solution. The excess solution was removed by zipping the bags shut and running over the bags with a rubber roller. The pooled excess solutions were removed with a paper towel. The bags were then vacuum-packed into Foodsaver™ bags. The bags were deliberately not purged of oxygen so as to minimize solvent evaporation. The samples were placed in an aluminum tote and exposed for 1 hour to Co-60γ radiation. The dose exposure corresponded to 5 kGy. The samples were taken out of the bags and washed with copious amounts of water to remove any traces of homopolymer. The completely washed samples were then air dried.

The diacetoneacrylamide grafted membranes were then converted to guanylhydrazone functional membranes. An aminoguanidine solution was prepared by dissolving 65 grams in 1 liter of methanol, and adding trifluoroacetic acid (2.25 mL). Each membrane was placed in a 500 mL polyethylene bottle, 100 mL of the aminoguanidine solution was added, the bottles were sealed, and the mixtures were placed on a roller at room temperature overnight. Excess solution was removed, and the membranes were washed extensively with deionized water and dried.

24 mm disks were punched out of the sheets and placed in a centrifuge tube. Bovine serum albumin solution (BSA, Sigma Aldrich) was prepared to a concentration of 0.75 mg/ml in 25 mM TRIS buffer, pH 8.0 (tris(hydroxymethyl) aminomethane, Sigma). 4.5 ml of the BSA solution was pipetted into each centrifuge tube, the tubes were capped, and the tubes were tumbled overnight. The supernatant solutions were analyzed by a UV-VIS spectrometer at 279 nm with background correction applied at 325 nm. Static binding capacities for the samples were found to be between 1 and 4 mg/mL. Analyses of the ungrafted substrates displayed binding capacities of <0.2 mg/mL.

TABLE

| | Substrate |
|---|---|
| Example 25 | Polyvinylidene fluoride membrane, 2 μm nominal pore size |
| Example 26 | Nylon 6 melt-blown non-woven web |
| Example 27 | Nylon 66 membrane, single reinforced layer nylon three zone membrane, nominal pore size 1.8 μm |
| Example 28 | Polypropylene non-woven web, sold as 3M Doodleduster ™ cloth |

Example 29

A 60 gsm nylon 6 meltblown nonwoven substrate with a 4.3 um effective fiber diameter and sample size of about 30 cm×43 cm (1290 $cm^2$ or 200 square inches) was purged of air and inserted into Ziploc bags in a glove box under nitrogen atmosphere (less than 20 ppm oxygen) and sealed. The Ziploc bag was then removed from the glove box, and irradiated to a dose level of 60 kGy (kilogray) by passing it through the electron beam. The bag was returned to the $N_2$ atmosphere-controlled glove box.

The Ziplock bag was opened and the nonwoven substrate was imbibed by pouring 150 grams of a nitrogen purged imbibing solution comprising; 17% diacetone acrylamide monomer, 10% polyethylene glycol with hydroxy end groups, average molecular weight 4,600 g/mole (PEG 4600), 1.0% Sartomer SR-550 PEG-acrylate and 72% water by weight inside the Ziploc bag with the nonwoven substrate. The nonwoven is kept flat and is completely and evenly saturated with a slight excess of grafting solution. The Ziploc bag is sealed. The Ziploc bag remains inside of the nitrogen filled glove box to allow sufficient time for all of the grafting monomer to graft-polymerize by free radical reaction with the nonwoven substrate. After a minimum of 6 hrs or as long as about 18 hrs (overnight), the grafted nylon nonwoven sample was removed from the glovebox and the Ziploc bag and the grafted nonwoven was washed three times by soaking in 2 liters of fresh DI water (to remove the PEG and any unreacted monomer) and then air dried to ambient conditions.

A solution of aminoguanidine (92 grams) and concentrated hydrochloric acid (3.45 mL) in deionized water (1500 mL total solution volume) was prepared. A sheet of the grafted nonwoven (ca. 12 cm×40 cm) was placed in a 1 gallon plastic jar. A portion (500 mL) of aminoguanidine solution was added to the jar, which was then sealed and placed on a roller for overnight reaction at room temperature. The excess aminoguanidine solution was decanted, the derivatized nonwoven sheet was rinsed under a stream or deionized water for 15 minutes, and the sheet then allowed to air dry at room temperature. A 24 mm diameter disk was cut from the coated web. This disk was placed in a 5 mL centrifuge tube, 4.5 mL of a Bovine serum albumin (BSA) solution (ca. 3 mg/mL in 25 mM TRIS, pH 8.0) was added, and the mixture tumbled at room temperature overnight. The UV absorbance of the supernatant solution was measured at 279 nm and compared to the absorbance prior to contact with the disk to determine the static binding capacity for BSA. The functionalized nonwoven was found to absorb 152 mg of BSA per gram of web.

Example 30

Using standard microbiological procedures, cultures of the following were prepared:
a) *Bacillus atrophaeous* (spores and cell debris)
b) *Clostridium sporogenes* (spores)
c) *Escherichia coli* (cells and cell debris)
d) Chinese hamster ovary (CHO) cells
e) Baker's yeast

When flocculation experiments were conducted similarly to those described in Example 17 on these mixtures, the ligand functional polymers of the invention consistently displayed good flocculating ability in the presence of sodium chloride concentrations in excess of 50 mM.

Example 31

Aminoguanidine hydrochloride (1.11 grams), methanol (15 grams), and acetoacetoxyethyl methacrylate (2.2 grams) were stirred at room temperature and monitored periodically by NMR. After stirring for 21 hours, NMR confirmed complete conversion of the methacrylate monomer to the corresponding guanylhydrazone hydrochloride

The invention claimed is:

1. A functionalized substrate comprising a porous base substrate and a grafted or ungrafted coating of a carbonyl-functional (co)polymer functionalized with pendent guanidinyl groups on the surface thereof,
said pendent guanidinyl groups are of the formula:

wherein
$R^1$ is H, $C_1$-$C_{12}$ alkyl, or $C_5$-$C_{12}$ (hetero)aryl,
$R^2$ is a covalent bond, a $C_2$ to $C_{12}$ alkylene, or a $C_5$-$C_{12}$ (hetero)arylene, $R^9$ is $C_2$ to $C_{12}$ alkylene or $C_5$-$C_{12}$ (hetero)arylene,
each $R^3$ is independently H, —OH, $C_1$-$C_{12}$ alkyl, or $C_5$-$C_{12}$ (hetero)aryl,
each $R^4$ is H, $C_1$-$C_{12}$ alkyl, $C_5$-$C_{12}$ (hetero)aryl, or —N($R^3$)$_2$.

2. The functionalized substrate of claim 1 wherein the pendent guanidinyl groups are of the formula:

wherein
$R^1$ is H, $C_1$-$C_{12}$ alkyl, or $C_5$-$C_{12}$ (hetero)aryl,
$R^9$ is $C_2$ to $C_{12}$ alkylene or $C_5$-$C_{12}$ (hetero)arylene,
each $R^3$ is independently H, —OH, $C_1$-$C_{12}$ alkyl, or $C_5$-$C_{12}$ (hetero)aryl,
each $R^4$ is H, $C_1$-$C_{12}$ alkyl, $C_5$-$C_{12}$ (hetero)aryl, or —N($R^3$)$_2$, preferably H, or $C_1$-$C_4$ alkyl,
$R^5$ is a divalent alkylene.

3. The functionalized substrate of claim 1 wherein the carbonyl-functional (co)polymer is selected from the group consisting of copolymers of; acrolein, vinyl methyl ketone, vinyl ethyl ketone, vinyl isobutyl ketone, diacetone (meth) acrylamide, acetonyl acrylate, carbon monoxide copolymer, and diacetone (meth)acrylate.

4. The functionalized substrate of claim 2 wherein the (co)polymer comprises polymerized monomer units of the formula:

VI wherein
$R^1$ is H, $C_1$-$C_{12}$ alkyl, or $C_5$-$C_{12}$ (hetero)aryl,
$R^2$ is a covalent bond, a $C_2$ to $C_{12}$ alkylene, or a $C_5$-$C_{12}$ (hetero)arylene, $R^9$ is $C_2$ to $C_{12}$ alkylene or $C_5$-$C_{12}$ (hetero)arylene, each $R^3$ is independently H, —OH, $C_1$-$C_{12}$ alkyl, or $C_5$-$C_{12}$ (hetero)aryl,

$R^4$ is H, $C_1$-$C_{12}$ alkyl, $C_5$-$C_{12}$ (hetero)aryl, or —N$(R^3)_2$, X is —O— or —NR$^3$—

$R^6$ is a $C_2$ to $C_{12}$ alkylene, and $R^7$ is H or $CH_3$.

5. The functionalized substrate of claim 2 where the (co)polymer comprises polymerized monomer units of the formula:

VII wherein $R^1$ is H, $C_1$-$C_{12}$ alkyl, or $C_5$-$C_{12}$ (hetero)aryl, $R^2$ is a covalent bond, a $C_2$ to $C_{12}$ alkylene, or a $C_5$-$C_{12}$ (hetero)arylene, $R^9$ is $C_2$ to $C_{12}$ alkylene or $C_5$-$C_{12}$ (hetero)arylene, each $R^3$ is independently H, $C_1$-$C_{12}$ alkyl, or $C_5$-$C_{12}$ (hetero)aryl, preferably H or $C_1$-$C_4$ alkyl, $R^4$ is H, $C_1$-$C_{12}$ alkyl, $C_5$-$C_{12}$ (hetero)aryl, or —N$(R^3)_2$, preferably H, or $C_1$-$C_4$ alkyl, and $R^7$ is H or $CH_3$.

6. The functionalized substrate of claim 2 where the (co)polymer further comprises hydrophilic monomer units.

7. The functionalized substrate of claim 2 wherein the (co)polymer has the formula:

-(M$^{Lig}$)$_y$-(M$^{Hydrophil}$)$_x$--(M$^{hydrophob}$)$_z$-(M$^{CO}$)$_{w*}$-, where -(M$^{CO}$)$_w$ are carbonyl functional monomer units having "w" polymerized monomer units, -(M$^{Hydrophil}$)$_x$- are hydrophilic monomer units having "x" polymerized monomer units, -(M$^{hydrophob}$)$_z$- are hydrophobic monomer units having "z" polymerized monomer units (M$^{Lig}$)$_y$ are ligand functional monomer units having "y" polymerized monomer units, y is 10 to 100 wt. % of the monomer units;

x is 0 to 90 wt. % of the monomer units; and w* may be comprise 0 to 90 wt. % of the monomer units, and z is 0 to 20 wt. %, based on 100 wt. % total monomers.

8. The functionalized substrate of claim 1 wherein the ligand-functionalized polymer is coated on the porous substrate.

9. The functionalized substrate of claim 1 wherein the ligand-functionalized polymer is grafted on the substrate.

10. The functionalized substrate of claim 1 wherein the porous base substrate is a microporous base substrate.

11. The functionalized substrate of claim 1 wherein the porous base substrate is a nonwoven web.

12. A method of separating a biological species from a fluid comprising contacting the fluid with the functionalized substrate of claim 1 whereby a complex comprising the functionalized substrate and the biological species is formed, and separating the complex.

13. The method of claim 12 wherein the biological species are selected from cells, cell debris, viruses, proteins, nucleic acids, and endotoxins.

14. The method of claim 12 where the functionalized substrate is selected from a particle, a fiber, a film, or a sheet.

15. The method of claim 12 where the functionalized substrate is a woven or nonwoven web.

* * * * *

UNITED STATES PATENT AND TRADEMARK OFFICE
CERTIFICATE OF CORRECTION

PATENT NO.       : 8,377,672 B2
APPLICATION NO.  : 12/986485
DATED            : February 19, 2013
INVENTOR(S)      : Jerald Kenneth Rasmussen

It is certified that error appears in the above-identified patent and that said Letters Patent is hereby corrected as shown below:

In the Specification:

Column 2,

Line 65, delete "  " and insert --  --.

Column 3,

Line 27-30, delete "  " and insert --  --.

Signed and Sealed this
Second Day of July, 2013

Teresa Stanek Rea
*Acting Director of the United States Patent and Trademark Office*